(12) United States Patent
    Jacob

(10) Patent No.: US 12,625,066 B2
(45) Date of Patent: May 12, 2026

(54) DETECTING A MIXTURE RATIO OF TWO COMPONENTS OF A TEXTILE FIBER STRUCTURE

(71) Applicant: Uster Technologies AG, Uster (CH)

(72) Inventor: Rainer Jacob, Fehraltorf (CH)

(73) Assignee: Uster Technologies, AG, Uster (CH)

( * ) Notice: Subject to any disclaimer, the term of this patent is extended or adjusted under 35 U.S.C. 154(b) by 196 days.

(21) Appl. No.: 18/551,298

(22) PCT Filed: Mar. 15, 2022

(86) PCT No.: PCT/CH2022/000002
     § 371 (c)(1),
     (2) Date: Sep. 19, 2023

(87) PCT Pub. No.: WO2022/198342
     PCT Pub. Date: Sep. 29, 2022

(65) Prior Publication Data
     US 2024/0175806 A1     May 30, 2024

(30) Foreign Application Priority Data

Mar. 26, 2021   (CH) ..................................... 00323/21

(51) Int. Cl.
     *G01N 21/25*        (2006.01)
     *G01N 21/17*        (2006.01)
                 (Continued)

(52) U.S. Cl.
     CPC ......... *G01N 21/255* (2013.01); *G01N 33/367* (2013.01); *G01N 2021/1774* (2013.01);
                 (Continued)

(58) Field of Classification Search
     CPC ...... G01N 21/255; G01N 21/31; G01N 21/94; G01N 33/367; G01N 2021/1774;
                 (Continued)

(56) References Cited

U.S. PATENT DOCUMENTS 5,737,076 A * 4/1998 Glaus ...................... G01J 3/457
                                              356/310
6,452,157 B1 * 9/2002 Hosel ................. G01N 21/8915
                                              250/227.16

(Continued)

FOREIGN PATENT DOCUMENTS

WO    WO-2011026249 A1 *  3/2011   ........ G01N 21/8915
WO    WO-2016055048 A1 *  4/2016   ................ G01J 3/28
WO    WO-2019051620 A1 *  3/2019   ............. D01H 13/32

OTHER PUBLICATIONS

Priore Ryan J et al. "Spectral imaging of chemical compounds using multivariate 6.9.10 optically enhanced filters integrated with InGaAs VGA cameras," SPIE, US vol. 9824, May 12, 2016 (May 12, 2016), pp. 98240P-98240P.

*Primary Examiner* — Octavia Hollington
(74) *Attorney, Agent, or Firm* — TechnicalAttorney; Rick Barnes

(57)            ABSTRACT

A device for detecting a mixture ratio of two components of a textile fabric contains a radiation source for transmitting electromagnetic radiation in a spectral band in the direction of the textile fiber structure, a radiation sensor for receiving at least a part of the electromagnetic radiation, and a spectral filter with spectral properties in the spectral band for filtering at least one part of the electromagnetic radiation. The transmittance of the spectral filter in the spectral band has at least one local maximum and at least one local minimum. The spectral properties of the spectral filter in the spectral band are adapted to the spectral properties of the radiation source and each of the two components such that a radiation intensity received by the radiation sensor is a monotonous function of the mixture ratio of the two components. The device is simple in design and allows the use of spatially resolving imaging radiation sensors.

16 Claims, 2 Drawing Sheets

Figure 1:
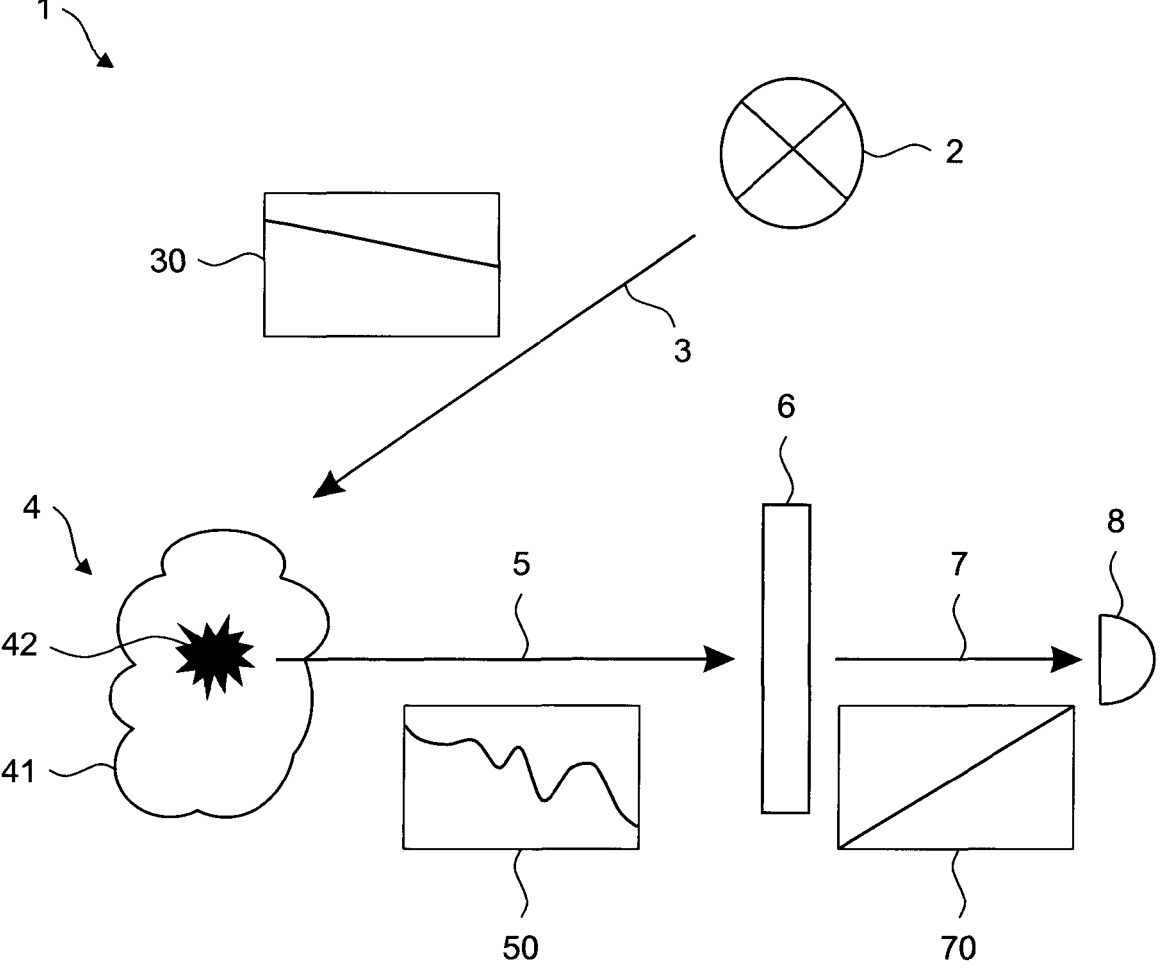

(51) Int. Cl.
    *G01N 21/94*         (2006.01)
    *G01N 33/36*         (2006.01)

(52) U.S. Cl.
    CPC .................. *G01N 2021/178* (2013.01); *G01N 2021/1789* (2013.01); *G01N 21/94* (2013.01)

(58) Field of Classification Search
    CPC ..... G01N 2021/178; G01N 2021/1789; G01N 2021/844; G01N 2201/068
    See application file for complete search history.

(56)                  References Cited

U.S. PATENT DOCUMENTS

| | | | |
|---|---|---|---|
| 7,962,187 B2 * | 6/2011 | Fantini ................ | A61B 5/0091 |
| | | | 600/475 |
| 10,175,109 B2 * | 1/2019 | Perkins ................. | G01N 21/31 |
| 11,402,335 B2 * | 8/2022 | Dehkordi ............. | G01N 33/365 |
| 2017/0241839 A1 | 8/2017 | Perkins | |
| 2018/0146855 A1 * | 5/2018 | Anikanov ................ | G01J 3/28 |
| 2020/0240769 A1 * | 7/2020 | Zuta ........................ | G06T 7/521 |
| 2021/0199593 A1 | 7/2021 | Dehkordi et al. | |

* cited by examiner

DETECTING A MIXTURE RATIO OF TWO COMPONENTS OF A TEXTILE FIBER STRUCTURE

FIELD OF THE INVENTION

The present invention is in the field of quality monitoring in the textile industry. It relates to a device and a method for detecting a mixture ratio of two components of a textile fiber structure, according to the independent claims. A preferred application is the detection of foreign materials in a textile fiber structure such as fiber flocks, fiber web, sliver, roving, yarn, woven fabric, knitted fabric, or nonwoven.

DESCRIPTION OF THE PRIOR ART

Foreign materials in the yarn represent one of the major problems of today's spinning mills. These are materials that differ from the base material of the yarn fibers, e.g. cotton fibers. They can be of various origins, such as residues of transport packaging (plastic packaging, cords), civilization impurities (soot parts, plastic bags) or residues of living beings (human or animal hair, plant stalks). Foreign materials cause thread breakage during spinning and weaving, take dye in a different way than the base material and affect the appearance of the final textile product. They significantly reduce the value of the final product. An overview of fabric defects caused by foreign materials and recommendations to reduce them is given in paragraph 3.8 of the USTER® NEWS BULLETIN NO. 47 "The origins of fabric defects— and ways to reduce them", Uster Technologies AG, March 2010.

Foreign materials can be detected and, if necessary, rejected at various stages of the yarn manufacturing process.

The blowroom process is part of the yarn manufacturing process and is upstream of the carding process. The aim is to prepare the raw material so that it can be fed to the carding process in as constant a quality as possible and free of impurities. It comprises the opening of the raw material, the feeding of the same into the processing operation, and the mixing and coarse cleaning of the fed material. Depending on the design of the process, individual work steps can be run through several times or even omitted. At this stage of the process, the material is in the form of fiber flocks (for example, in the case of cotton and wool) or shreds (in the case of synthetic fiber material). The material is transported by an air stream that connects the various units in the blowroom process.

The spinning process is another part of the yarn manufacturing process and is indirectly or directly downstream of the carding process. In this process, the yarn as the end product is spun from a sliver, e.g., the intermediate product of a carding machine, or a roving. In the process, the roving or sliver is transformed into its final form, the yarn, by drawing and twisting. During spinning, the yarn is wound onto spindles. Subsequently, the spindles are rewound onto large bobbins. The material is transported in the form of spindles and bobbins.

The purification of foreign materials can basically be divided into the following three steps:

1) Detection of the foreign material;
2) Spatial/temporal localization of the foreign material within the test material; and
3) Ejection of the foreign material.

In the blowroom process, foreign material cleaning can be carried out manually before the raw material is fed to the automatic converting process, or cleaning can be carried out automatically by appropriate equipment within the blowroom process. Nowadays, automatic cleaning is common.

In the case of automatic cleaning, detection and localization are carried out with the aid of detection devices which recognize differences in a certain characteristic within the material flow. The following are mentioned in a non-exhaustive way here: reflection and transmission of electromagnetic radiation or fluorescence. In the simplest applications, optical detection devices are used to mimic the human eye and analyze the color impression of the material stream, detecting corresponding color differences. U.S. Pat. No. 6,452,157 B1 discloses a device for detecting impurities, foreign materials and foreign fibers in textile fiber material. The device has at least two light sources which alternately illuminate the fiber material with different colors. Furthermore, a sensor is provided which receives the colors of the light reflected from the fiber material.

However, for the detection of foreign materials that are transparent to visible light or have a similar color to the raw material, more sophisticated detection devices are needed. In this case, the material flow can be analyzed with the help of such electromagnetic radiation which is not perceived by the human eye (ultraviolet or infrared). In this case, the material affiliation is determined on the basis of characteristic signatures (for example, sequence of specific absorption bands) in the reflected or transmitted spectrum of the electromagnetic radiation. The more characteristics (e.g., absorption bands) within the signature are used for discrimination, the more accurate the discrimination of the characteristic signatures becomes. Currently, each characteristic within the signature requires a dedicated sensor within the detection device, so it only responds to the presence/absence of that one characteristic. The more characteristics that are to be used, the more complex the detection device becomes. The input signal must be split accordingly to the number of sensors and thus loses intensity. Furthermore, for certain characteristics there are currently no spatially, but only temporally resolving sensors. This requires a device upstream of the detection device that links time and location. Alternatively, the incident electromagnetic radiation can be modulated in time to match the characteristics. However, for the non-visible range of the electromagnetic spectrum, this is sometimes associated with great effort.

When distinguishing the material on the basis of color differences, as is common in the spinning process, the characteristics mentioned lie in the visible spectral range. Since the color impression is also due to the specific reflection/transmission of certain parts of the irradiated wavelength spectrum, each characteristic must also be detected individually in this case. For this purpose, either a temporal color modulation of the input signal can be performed, or the output signal modified by the yarn must be decomposed into the individual characteristics, as already explained. In the former case the spatial resolution deteriorates, in the latter the signal-to-noise ratio. The more colors are used, the greater the effect of these disadvantages. For this reason, processes have become established in practice that use only one or at most two colors. A yarn clearer that scans the yarn with several differently colored light components is known from WO-2011/026249 A1.

Multivariate optical filters are a special category of optical transmission filters or reflection filters. The filter characteristics of multivariate optical filters are adapted to a specific chemical signature. Different characteristics of the signature can be used simultaneously and independently in a single filter. Multivariate optical elements thus allow material identification based on the chemical signature. If the input signal to the filter exactly matches the matched signature, the signal passes through the multivariate optical filter unimpeded. If the input signal deviates from the signature, it is attenuated as it passes through the filter. The greater the deviation, the greater the attenuation. Multivariate optical filters, in addition to discriminating materials, also allow a mixture ratio to be determined based on the chemical signature that is altered by the mixing. The specific transmittance or reflectance of multivariate optical filters is obtained from the chemical signatures of the materials to be discriminated using the partial least squares method.

SUMMARY OF THE INVENTION

It is the object of the present invention to provide a device for detecting a mixture ratio of two components of a textile fiber structure, which avoids the above disadvantages. In particular, the device is to be of simple construction. It is intended to provide high spatial resolution and the use of imaging, spatially resolving radiation sensors. At the same time, the signal-to-noise ratio shall be high. A further object is to provide a corresponding method for detecting a mixture ratio of two components of a textile fiber structure.

These and other objects are solved by the device and method according to the invention, as defined in the independent claims. Advantageous embodiments are indicated in the dependent claims.

The invention is based on the idea of designing a spectral filter specifically with respect to the components of the textile fiber structure, so that a radiation intensity received by the radiation sensor is a monotonous function of the mixture ratio of the two components. Furthermore, the transmittance or reflectance in the spectral band under consideration is to have at least one local maximum and at least one local minimum such that multiple characteristic wavelengths are considered. Furthermore, the invention comprises that said spectral filter can also be designed for the ratio of different characteristics, e.g. color impressions, and thus also makes color differences of materials of the same type detectable without signal loss.

The design of the spectral filter is based on the specific chemical and/or color signatures of the two components. As an example, individual characteristics may be enhanced by high transmission while other characteristics are attenuated by low transmission. The combination of amplification and attenuation in the spectral filter allows the mixture ratio of the two components to be determined based on the signal exiting the spectral filter. As an example, materials and/or colors for which the spectral filter has been optimized would produce a high output signal, whereas unoptimized materials and/or colors would cause a low output signal.

The device according to the invention is used for detecting a mixture ratio of two components of a textile fiber structure. It includes a radiation source for transmitting electromagnetic radiation in a spectral band toward the textile fiber structure for interaction with the textile fiber structure. Further, the device includes a radiation sensor for receiving at least a part of the electromagnetic radiation after interaction with the textile fiber structure. The device also includes a spectral filter having spectral properties in the spectral band for filtering at least a part of the electromagnetic radiation before or after interaction with the textile fiber structure. The transmittance or reflectance of the spectral filter in the spectral band has at least one local maximum and at least one local minimum. The spectral properties of the spectral filter in the spectral band are adapted to the spectral properties of the radiation source and each of the two components such that a radiation intensity received by the radiation sensor is a monotonous function of the mixture ratio of the two components.

In one embodiment, the at least one local maximum lies at the wavelength or wavelengths of the electromagnetic radiation at which the absolute value of the difference in the absorptance, transmittance, or reflectance of the two components has a local maximum.

In one embodiment, the transmittance or reflectance of the spectral filter in the spectral band has at least two local maxima and local minima each.

The spectral filter can be designed as a reflection filter or as a transmission filter.

In one embodiment, the spectral filter is designed as an interference filter.

In one embodiment, the spectral filter is integrated into the radiation sensor.

In one embodiment, the radiation sensor is spatially resolving and/or time resolving. It can be designed, for example, either as a digital camera with a two-dimensional image converter or as a one-dimensional line sensor.

The method according to the invention is used for detecting a mixture ratio of two components of a textile fiber structure. Electromagnetic radiation in a spectral band is transmitted from a radiation source in the direction of the textile fiber structure. At least a part of the electromagnetic radiation interacts with the textile fiber structure. At least a part of the electromagnetic radiation is received by a radiation sensor after interacting with the textile fiber structure. At least a part of the electromagnetic radiation is filtered by a spectral filter having spectral properties in the spectral band before or after interacting with the textile fiber structure. The spectral filter is selected such that its transmittance or reflectance in the spectral band has at least one local maximum and at least one local minimum, and its spectral properties in the spectral band are adapted to the spectral properties of the radiation source and each of the two components in the textile fiber structure such that a radiation intensity received by the radiation sensor is a monotonous function of the mixture ratio of the two components.

In one embodiment, one of the two components is a base material that makes up a predominant portion of the textile fiber structure, and the other of the two components is a foreign material whose proportion in the textile fiber structure is determined.

In the device and method, the spectral band may be, for example, in the wavelength range between 300 nm and 2200 nm, and preferably in the wavelength range between 700 nm and 1900 nm.

For example, in the device and method, the spectral band may have a width between 200 nm and 500 nm.

The radiation source may include a single radiation element, e.g., a halogen lamp. Alternatively, it may include multiple radiation elements, e.g., a halogen lamp and a mercury vapor lamp.

The expressions "local maximum", "local minimum" and "monotone function" used in this specification are used in the sense of their respective mathematical meanings. They are known to the person skilled in the art and their definitions can be taken from textbooks or reference works on mathematics.

The device and method according to the invention allow a simple yet reliable determination of a mixture ratio of two components of a textile fiber structure. They avoid splitting the incoming electromagnetic radiation reflected or transmitted by the textile fiber structure among multiple radiation sensors. The device is simple in design and allows the use of imaging, spatially resolving radiation sensors. It does not require temporal modulation of the input signal, thus achieving high spatial resolution.

ENUMERATION OF THE DRAWINGS

In the following, an embodiment of the invention is explained in detail with reference to the drawings. For the sake of a clearer illustration, an application is described in which a proportion of a foreign material in a base material of a textile fiber structure is determined. However, this is not intended to limit the generality of the invention, which relates to the determination of a mixture ratio of two components of a textile fiber structure.

FIG. 1 schematically shows an embodiment of the device according to the invention.

FIG. 2 shows various spectra in a common spectral band, namely: (a) relative intensity distribution of a halogen lamp; (b) absorptance of cotton; (c) absorptance of polyethylene; and (d) transmittance of a spectral filter.

DETAILED DESCRIPTION OF THE INVENTION

An embodiment of the device 1 according to the invention is shown schematically in FIG. 1. It includes at least one broadband radiation source 2 for generating electromagnetic radiation 3. The generated electromagnetic radiation 3 has a spectral intensity distribution 30 characteristic of the radiation source 2. In FIG. 1, the intensity distribution 30 is shown as a schematic diagram in which the intensity is plotted as a function of wavelength.

At least a part of the electromagnetic radiation 3 generated by the radiation source 2 impinges on a textile fiber structure 4 to be examined. The textile fiber structure 4 can be, for example, one or more fiber flocks, a fiber web, a sliver, a roving, a yarn, a woven fabric, a knitted fabric, or a nonwoven. In the example of FIG. 1, without limiting the generality, a fiber flock is schematically drawn as textile fiber structure 4.

The textile fiber structure 4 contains two different components 41, 42. Without limiting generality, it is assumed here for illustrative purposes that the textile fiber structure 4 consists of a base material 41, e.g., cotton, and may possibly contain one or more foreign materials 42 that differ from the base material 41. When the electromagnetic radiation 3 impinges on the textile fiber structure 4, there is an interaction of the electromagnetic radiation 3 with the base material 41 and, if present, the foreign material 42. As a result of the interaction, the intensity distribution 30 of the electromagnetic radiation 3 is changed according to the chemical or color characteristics of the materials. Radiation 5 reflected or transmitted at the textile fiber structure 4 thus has a spectral intensity distribution 50 that differs from the intensity distribution 30 of the radiation 3 impinging on the textile fiber structure 4. The intensity distribution 50 is again shown in FIG. 1 as a schematic diagram in which the intensity is plotted as a function of wavelength.

After interaction with the textile fiber structure 4, the electromagnetic radiation 5 interacts with a spectral filter 6 in the exemplary embodiment of FIG. 1. The interaction can occur by means of transmission or reflection at the spectral filter 6. The spectral properties of the spectral filter 6 are specifically matched to a type or class of foreign material 42. The spectral filter 6 may be designed as an interference filter, for example. It changes the intensity distribution 50 of the electromagnetic radiation 5 interacting with it in such a way that differences between the base material 41 and the foreign material 42 are amplified.

If the spectral intensity distribution 50 before the spectral filter 6 corresponds to that of the base material 41, then the intensity of a radiation 7 after the spectral filter 6 should be minimal, for example. If, on the other hand, the spectral intensity distribution 50 upstream of the spectral filter 6 corresponds to that of the foreign material 42, the intensity of radiation 7 downstream of the spectral filter 6 shall be, for example, a maximum. If the spectral intensity distribution 50 before the spectral filter 6 has characteristics of both materials 41 and 42, the intensity of the radiation 7 after the spectral filter 6 shall correspond to a monotonous function of the mixture ratio of the materials 41 and 42. This is schematically illustrated in FIG. 1 by a diagram 70 showing an intensity of radiation 7 after interaction with spectral filter 6 as a function of the proportion of foreign materials 42 in textile fiber structure 4.

The spectral filter 6 thus converts the incident wavelength-dependent intensity distribution 50 into an intensity distribution 70 that is a monotonous function of the mixture ratio of the two components 41 and 42. The intensity of the electromagnetic radiation 7 present after the spectral filter 6 is thus a measure of the mixture ratio. In the example discussed here, it is a measure of the presence and amount of the foreign material 42 in the textile fiber structure 4 and/or of the degree of color variation between the base material 41 and the foreign material 42.

After interaction with the spectral filter 6, electromagnetic radiation 7 is detected by a broadband radiation sensor 8. In a preferred embodiment, the radiation sensor 8 is spatially resolving, and the textile fiber structure 4 is imaged onto the radiation sensor 8 by means of optics (not drawn in). This also provides information about the number, size, and shape of the foreign materials 5 present in the textile fiber structure 4. The radiation sensor 8 is preferably time-resolving. It can be designed, for example, as a digital camera.

In an image of the textile fiber structure 4 taken by the radiation sensor 8, foreign materials 42 appear bright against a dark background in the present example.

In an alternative embodiment, the spectral properties of the spectral filter 6 can be matched to the radiation source 2, the base material 41 and/or the foreign material 42 in such a way that the intensity of the radiation 7 after the spectral filter 6 is at a maximum when the textile fiber structure 4 consists only of the base material 41, and decreases as the proportion of foreign material 42 increases. In this case, foreign materials 42 appear dark against a light background.

In another embodiment, the spectral filter 6 can be inserted in the beam path between the radiation source 2 and the textile fiber structure 4. In this case, the electromagnetic radiation 3 generated by the light source 2 first interacts with the spectral filter 6 and then impinges on the textile fiber structure 4. The effect is analogous and an image of the textile fiber structure 4 recorded by the radiation sensor 8 corresponds substantially to the images recorded according to the embodiments described above.

Figure 2A:
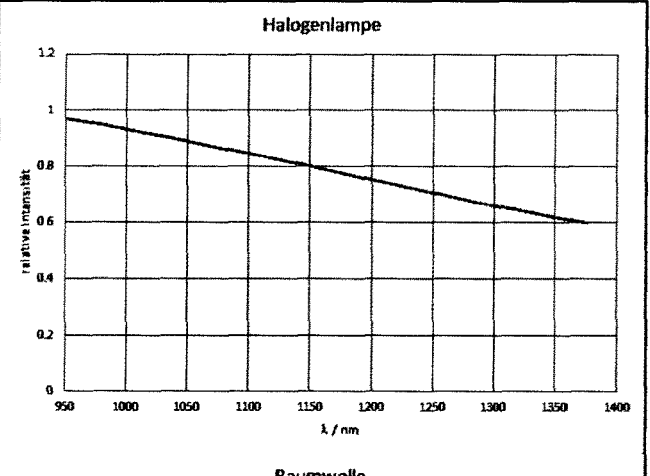

FIG. 2(a) shows an example of the relative intensity of the electromagnetic radiation 3 generated by a halogen lamp 2 as a function of the radiation wavelength A. In the spectral band shown (950 nm≤λ≤1400 nm, near and shortwave infrared), the relative intensity decreases monotonously with the radiation wavelength A. For other light sources 2, the intensity spectrum may look different.

Figure 2B:
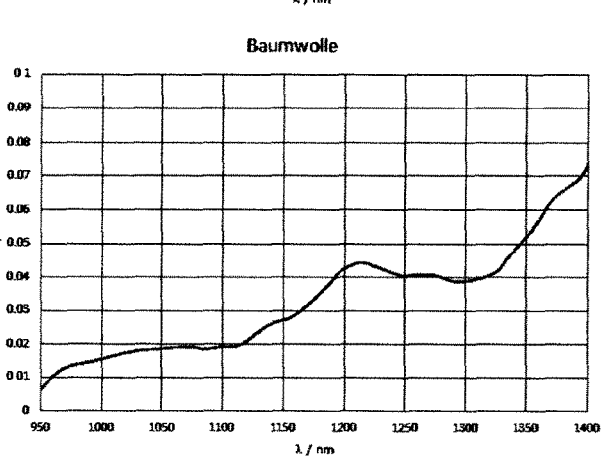
Figure 2C:
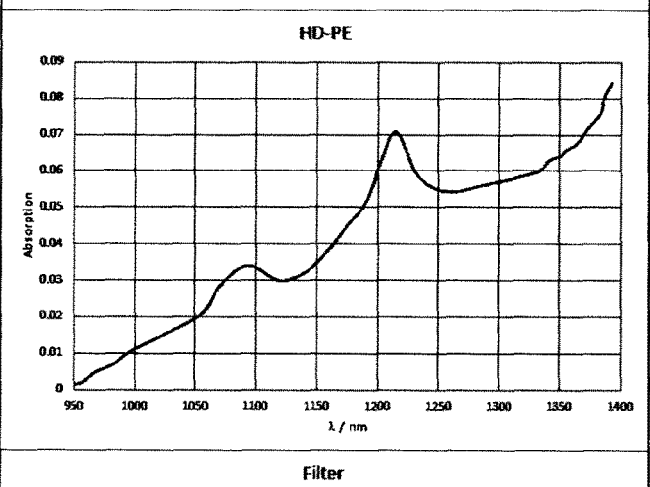
Figure 2D:
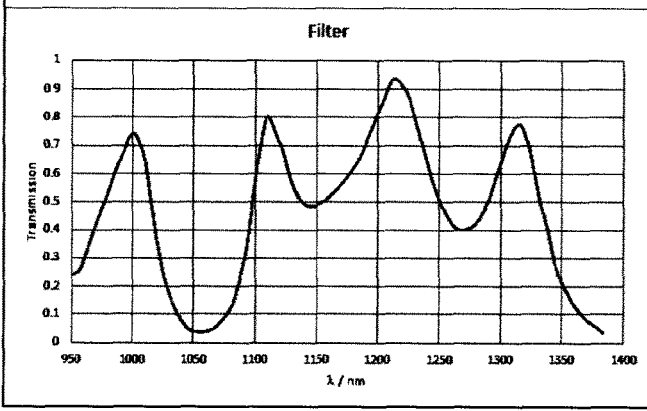

FIGS. 2(b) and 2(c) show absorption spectra of cotton, which is a typical textile base material 41, and polyethylene, which can be a foreign material 42, respectively. The respective absorptance is again plotted as a function of the radiation wavelength λ in the same spectral band as in FIG. 2(*a*).

The spectral properties of the spectral filter 6 are determined by multidimensional variation calculation from the spectral intensity distribution 30 of the radiation source 2 as well as from spectral properties—absorptance, reflectance and/or transmittance—of the base material 41 and the foreign material 42 to be detected. The regression vector resulting from the multidimensional variation calculation contains a weighting for each wavelength in the spectral band under consideration. The weightings correspond to the transmittance or reflectance of the spectral filter 6 for the wavelengths in question. Thus, the spectral filter 6 is optimized for the detection of a particular foreign material 42 in a particular base material 41 when illuminated by a particular radiation source 2. Such methods for designing a spectral filter are known per se; an example can be found in the article "PLS-regression: a basic tool of chemometrics" by S. Wolda, M. Sjöströma, and L. Eriksson, Chemometrics and Intelligent Laboratory Systems, Volume 58, Issue 2, Oct. 28, 2001, pages 109-130.

FIG. 2(*d*) shows an exemplary transmittance of a spectral filter 6 as a function of the radiation wavelength λ in the same spectral band as in FIGS. 2(*a*)-2(*c*). In the example shown, the spectral filter 6 has four local maxima (at wavelengths of about λ≈1000 nm, 1110 nm, 1213 nm, and 1317 nm) and three local minima (at wavelengths of about λ≈1055 nm. 1145 nm, and 1268 nm) in the spectral band under consideration (950 nm≤λ≤1400 nm). The spectral filter 6 enhances the differences in absorption of cotton (FIG. 2(*b*)) and polyethylene (FIG. 2(*c*)), which is particularly evident at the wavelengths of about λ≈1100 nm, 1210 nm, and 1320 nm in the respective spectra.

By optimizing the transmission or reflection of the spectral filter 6 for the foreign material 42, those portions of the electromagnetic radiation 5 incident on the spectral filter 6 that result from the interaction of the radiation 5 with the foreign material 42 can pass through the spectral filter 6 unattenuated. Portions resulting from the base material 41 are attenuated by the spectral filter 6. The signal on the radiation sensor 8 is thus high for the foreign material 42 and low for the base material 41. If the radiation sensor 8 is designed as an image sensor, the foreign material 42 appears as bright image areas and the base material 41 as dark image areas on the image generated by the radiation sensor 8. It is understood that the present invention is not limited to the embodiments discussed above. With knowledge of the invention, the person skilled in the art will be able to derive further variants which also form part of the subject matter of the present invention.

LIST OF REFERENCE SIGNS

1 Device according to the invention
2 Radiation source
3 Electromagnetic radiation generated by the radiation source
30 Spectral intensity distribution
4 Textile fiber structure
41 Base material of the textile fiber structure
42 Foreign material in the textile fiber structure
5 Radiation reflected or transmitted by the textile fiber structure
50 Spectral intensity distribution
6 Spectral filter
7 Radiation after the spectral filter

70 Intensity of the detected radiation as a function of the proportion of foreign materials
8 Radiation sensor

The invention claimed is:

1. A device for detecting a mixture ratio of two components of a textile fiber structure, containing:
   a radiation source for transmitting electromagnetic radiation in a spectral band in a direction of the textile fiber structure for interaction with the textile fiber structure,
   a radiation sensor for receiving at least one part of the electromagnetic radiation after interaction with the textile fiber structure, and
   a spectral filter having spectral properties in the spectral band for filtering at least a part of the electromagnetic radiation before or after interaction with the textile fiber structure,
   wherein
   a transmittance or a reflectance of the spectral filter in the spectral band has at least one local maximum and at least one local minimum, and
   the spectral properties of the spectral filter in the spectral band are adapted to the spectral properties of the radiation source and each of the two components such that a radiation intensity received by the radiation sensor is a monotonous function of the mixture ratio of the two components.

2. The device according to claim 1, wherein the at least one local maximum lies at a wavelength or wavelengths of the electromagnetic radiation at which an absolute value of a difference of an absorptance, a transmittance, or a reflectance of the two components has a local maximum.

3. The device according to claim 1, wherein a transmittance or a reflectance of the spectral filter in the spectral band has at least two local maxima and local minima each.

4. The device according to claim 1, wherein the spectral filter is designed as a reflection filter or as a transmission filter.

5. The device according to claim 1, wherein the spectral filter is designed as an interference filter.

6. The device according to claim 1, wherein the spectral filter is integrated into the radiation sensor.

7. The device according to claim 1, wherein the spectral band is in a wavelength range between 300 nm and 2200 nm.

8. The device according to claim 1, wherein the spectral band has a width between 200 nm and 500 nm.

9. The device according to claim 1, wherein the radiation sensor is spatially resolving and/or time resolving.

10. The device according to claim 9, wherein the radiation sensor is formed either as a digital camera with a two-dimensional image converter or as a one-dimensional line sensor.

11. The device according to claim 1, wherein the spectral band is in a wavelength range of between 700 nm and 1900 nm.

12. A method for detecting a mixture ratio of two components of a textile fiber structure, wherein:
   electromagnetic radiation in a spectral band is transmitted from a radiation source in a direction of the textile fiber structure,
   at least a part of the electromagnetic radiation interacts with the textile fiber structure,
   at least a part of the electromagnetic radiation is received by a radiation sensor after interacting with the textile fiber structure, and

at least a part of the electromagnetic radiation is filtered by a spectral filter with spectral properties in the spectral band before or after interacting with the textile fiber structure, wherein, the spectral filter is selected such that, a transmittance or a reflectance in the spectral band has at least one local maximum and at least one local minimum, and its spectral properties in the spectral band are adapted to the spectral properties of the radiation source and each of the two components in the textile fiber structure such that a radiation intensity received by the radiation sensor is a monotonous function of the mixture ratio of the two components.

13. The method according to claim 12, wherein the spectral band is in a wavelength range between 300 nm and 2200 nm.

14. The method according to claim 12, wherein the spectral band has a width between 200 nm and 500 nm.

15. The method according to claim 12, wherein one of the two components is a base material of which a predominant part of the textile fiber structure consists, and the other of the two components is a foreign material whose proportion in the textile fiber structure is determined.

16. The method according to claim 12, wherein the spectral band is in a wavelength range of between 700 nm and 1900 nm.

* * * * *